(12) United States Patent
Anderson et al.

(10) Patent No.: US 8,758,417 B2
(45) Date of Patent: Jun. 24, 2014

(54) ADJUSTABLE STERNAL CLAMP ARRAY

(76) Inventors: Charles A. Anderson, Tacoma, WA (US); Shawn M. Burke, Jacksonville, FL (US); Michael Teague, Jacksonville, FL (US)

( * ) Notice: Subject to any disclaimer, the term of this patent is extended or adjusted under 35 U.S.C. 154(b) by 621 days.

(21) Appl. No.: 12/462,550

(22) Filed: Aug. 5, 2009

(65) Prior Publication Data
US 2011/0034958 A1 Feb. 10, 2011

(51) Int. Cl.
*A61B 17/04* (2006.01)
*A61B 17/84* (2006.01)
*A61F 2/08* (2006.01)

(52) U.S. Cl.
USPC ........... 606/324; 606/326; 606/328; 606/330; 606/905

(58) Field of Classification Search
USPC ............. 606/250, 251, 252, 258, 324, 70, 71, 606/75, 105, 282, 326, 328, 330, 280, 905
See application file for complete search history.

(56) References Cited

U.S. PATENT DOCUMENTS

| | | | |
|---|---|---|---|
| 3,473,528 A | 10/1969 | Mishkin et al. | |
| 4,201,215 A | 5/1980 | Crossett et al. | |
| 4,279,248 A | 7/1981 | Gabbay | |
| 4,327,715 A * | 5/1982 | Corvisier | 606/71 |
| 4,583,541 A | 4/1986 | Barry | |
| 5,139,498 A | 8/1992 | Astudillo Ley | |
| 6,051,007 A | 4/2000 | Hogendijk et al. | |
| 6,217,580 B1 | 4/2001 | Levin | |
| 6,238,396 B1 * | 5/2001 | Lombardo | 606/86 A |
| 6,302,899 B1 | 10/2001 | Johnson et al. | |
| 6,540,769 B1 | 4/2003 | Miller, III | |
| 6,712,821 B2 | 3/2004 | Gabbay | |
| 2006/0241591 A1* | 10/2006 | Biscup et al. | 606/60 |
| 2007/0038218 A1* | 2/2007 | Grevious | 606/71 |

* cited by examiner

*Primary Examiner* — Andrew Yang
*Assistant Examiner* — Diana S Jones
(74) *Attorney, Agent, or Firm* — Thomas C. Saitta; Stephen E. Kelly; Rogers Towers, P.A.

(57) ABSTRACT

A sternal closure clamp device assembly for securing and retaining longitudinally divided halves of a sternum, the assembly having at least two sternal clamps retained by clamp receiving members, the clamp receiving members being joined by a linking assembly whereby the distance between the clamps can be adjusted and fixed.

17 Claims, 5 Drawing Sheets

ADJUSTABLE STERNAL CLAMP ARRAY

BACKGROUND OF THE INVENTION

This invention generally relates to devices used to rejoin a human sternum that has been severed longitudinally, and more particularly relates to such devices that function in a clamping manner to retain the severed sternum portions in a closed and abutting relationship post-operatively.

It is often necessary in surgical operations to longitudinally sever the patient's sternum so that the ribs may be spread to provide access to internal organs such as the heart. It is then necessary to secure the sternum halves together for post-operative recovery. Various closure techniques are used to accomplish this task. For example, holes may be drilled into the sternum halves and suture material passed through and tightened to cinch the sternum halves together. Apertured plates may be added to further rigidify the sternum post-operatively, with the suture material being passed through the apertures in the plate and the sternum. Encircling members may be wrapped around the sternum and tightened. Toothed bridging members extending across the cut line may be pressed into the sternum surfaces and/or secured with threaded rods extending between the sternal halves.

Another sternal closure technique involves the use of expandable and contractible clamps having hook-like projections or engagement members on both ends, the clamp being positioned laterally relative to the sternal incision with the projections being disposed between adjoining rib pairs. The clamp is then linearly contracted or compressed to shorten the device and force the sternal halves together, the clamp typically comprising two members joined in a linear telescoping manner. Locking or securing means, either permanent or releasable, maintain the clamp in the contracted configuration.

Examples of such techniques and devices are described in U.S. Pat. No. 3,473,528 to Mishkin et al., U.S. Pat. No. 4,201,215 to Crossett et al., U.S. Pat. No. 4,279,248 to Gabbay, U.S. Pat. No. 4,583,541 to Barry, U.S. Pat. No. 5,139,498 to Astudillo Ley, U.S. Pat. No. 6,051,007 to Hogendijk et al., U.S. Pat. No. 6,217,580 to Levin, U.S. Pat. No. 6,302,899 to Johnson et al., U.S. Pat. No. 6,540,769 to Miller, III, and U.S. Pat. No. 6,712,821 to Gabbay.

While sternal clamps have proven very useful in stabilizing and rejoining a longitudinally severed sternum, there are situations where it would be beneficial to stabilize, rigidify and fix multiple sternal clamps relative to each other, such that in addition to clamping the sternum transversely the sternum is also longitudinally braced. It is an object of this invention to provide an array of sternal closure clamp devices that are joined together in the longitudinal direction parallel to the sternum such that a rigid framework or scaffold results. It is a further object to provide such an array where the separation distance between adjoining sternal clamps is adjustable in order to optimize the separation distance between adjoining sternal clamps.

SUMMARY OF THE INVENTION

The invention is in general an array of sternal closure clamp devices for post-operatively closing, securing and supporting a patient's sternum that has been longitudinally severed into two sternal halves. Each of the sternal clamps generally comprises a pair of slidingly interconnected body members that together form an expandable clamp, with one or more rearward-extending engagement members disposed on the outer end of one of the body members and one or more rearward-extending engagement members disposed on the outer end of the other body member. The engagement members are means to engage, secure or otherwise retain the sternal halves in an abutting relationship, with the engagement members having hooks, projections, fingers or the like disposed on their ends, whereby with the sternal clamps extending across the two sternal halves, the engagement members can be disposed against the outer edges of the sternal halves and between adjoining ribs to secure the sternal halves in an adjoining manner.

Each of the adjoining sternal clamps are joined in the longitudinal direction (i.e., the direction parallel to the longitudinal axis of the sternum) by a linking assembly that defines a framework or scaffold for rigidly linking each of the sternal clamps in a fixed manner. Most preferably, the linking assembly comprises means for adjusting the distance between adjoining sternal clamps.

Alternatively, in the case of a transverse cut through the sternum, the array can be oriented such that sternal clamps extend between rib pairs on either side of the sternum and the engagement members are disposed against the ribs themselves instead of the sternum.

DETAILED DESCRIPTION OF THE INVENTION

Figure 1:
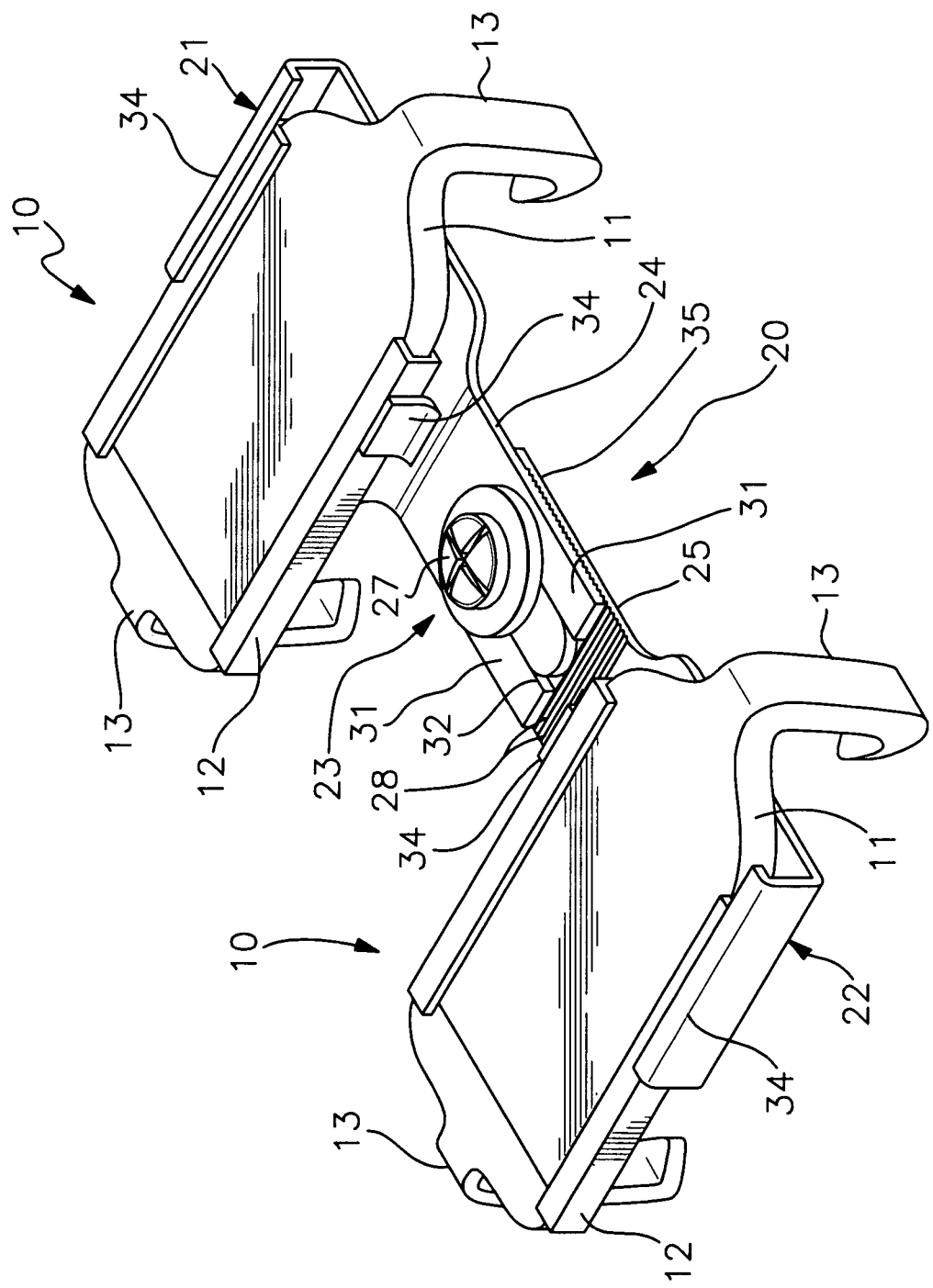
FIG. 1 is a perspective view of an array containing a pair of sternal clamps.

With reference to the drawings, the invention will now be described in detail with regard for the best mode and the preferred embodiment. The invention is an adjustable sternal closure clamp array used to close, secure and support a sternum post-operatively, the sternum having been severed longitudinally into left and right lateral sternal halves to provide access to the interior of the chest. The array insures that the sternum is stabilized laterally, such that the two sternal halves are pressed together, and longitudinally, such that the distance between adjoining sternal clamps remains fixed. In the preferred embodiment, the longitudinal distance between adjoining sternal clamps is adjustable to account for variation in patient size and other factors.

The sternal clamps presented in the drawings are of the type of sternal clamp set forth in U.S. Publication No. US20060167458A1, the disclosure of which is incorporated herein by reference. These clamps are utilized as representations for any sternal clamp. It is to be understood however that the particular embodiment or structure of the sternal clamps of the invention is not limited to this particular type, structure or style.

Figure 2:
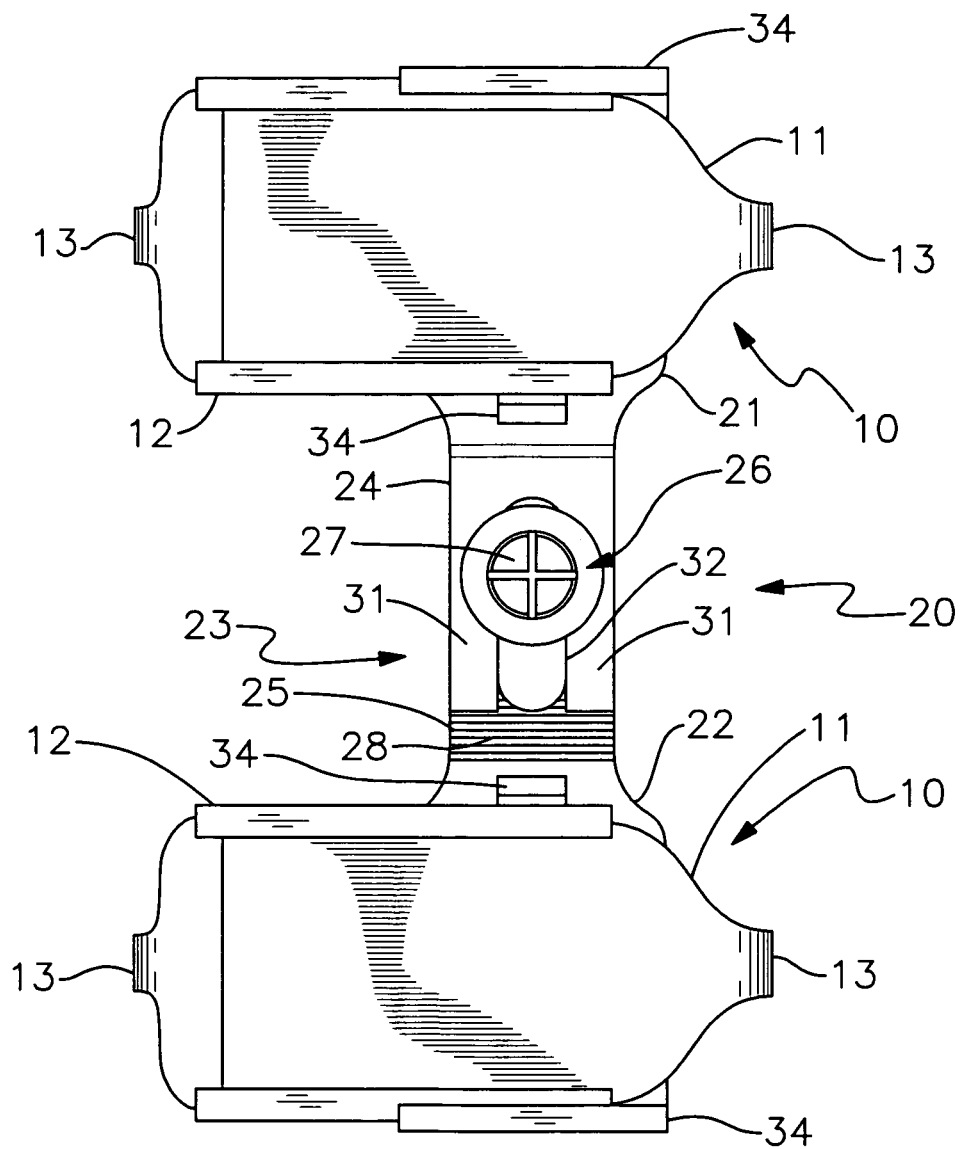
FIG. 2 is a front view of the array embodiment of FIG. 1.
Figure 3:
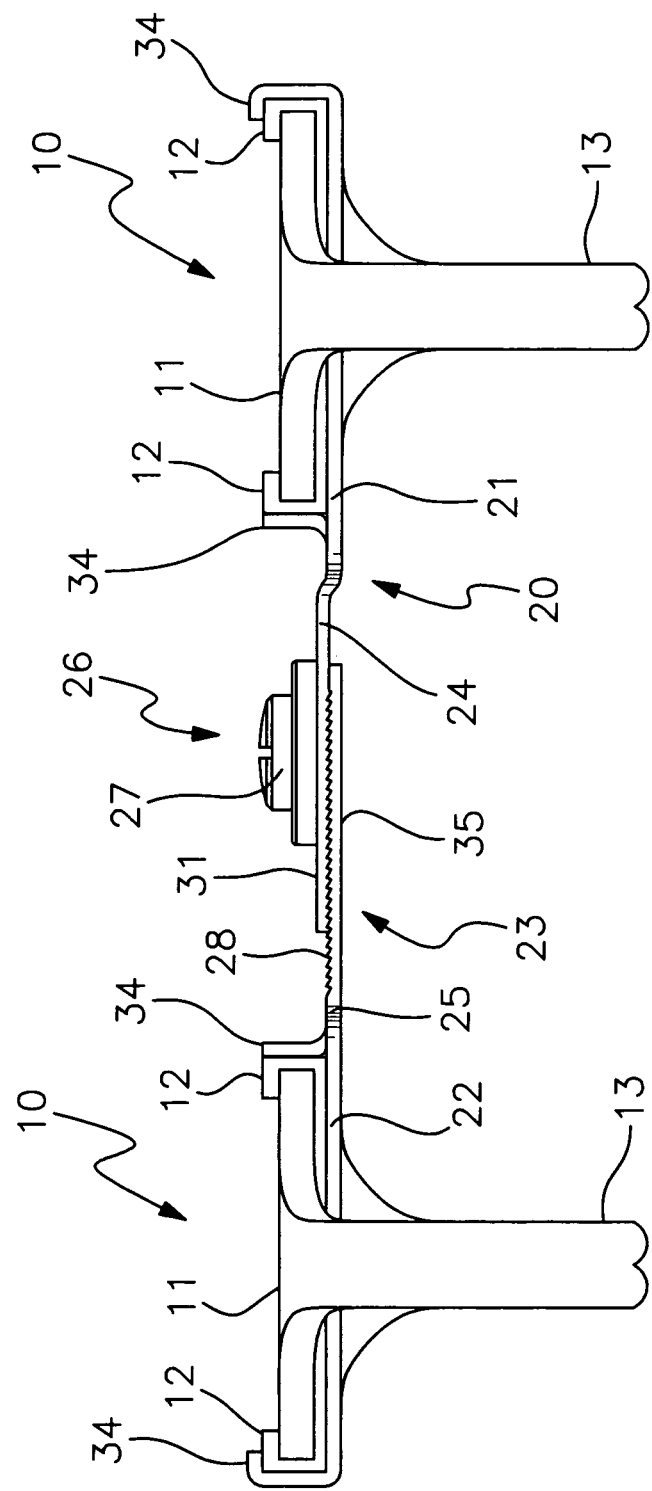
FIG. 3 is a side view of the array embodiment of FIG. 1.

FIGS. 1 through 3 illustrate a paired array wherein two sternal clamps 10 are joined by a linking assembly 20. The sternal clamps 10 each comprise a first sliding member 11 and a second sliding member 12, with projection members 13 extending rearward from the outer ends of each sliding member 11 and 12. This type of sternal clamp structure is well known in the art, and allows the sternal clamps 10 to be expanded such that the projection members 13 can be inserted between ribs and to the outside of the sternal halves. The clamps 10 are then contracted to force the sternal halves into abutment.

The linking assembly 20 may be an integral member of fixed dimension, but most preferably is an assembly adjustable in length longitudinally, such that the distance between the sternal clamps 10 can be altered as required. The linking assembly 20 as shown in FIGS. 1-3 comprises a first clamp receiving member 21 and a second clamp receiving member 22, each having paired flanges 34 that secure and retain the sternal clamps 10. Alternative means for retaining the sternal clamps 10, such as through the use of fastening members, mechanical interlocks or the like, could also be utilized. Linking assembly adjustment means 23 for adjusting the length of the linking assembly 20 are provided, and may comprise as shown a first bridging member 24 and a second bridging member 25 which cooperate in a telescoping or sliding relationship to connect the clamp receiving members 21 and 22, whereby the separation distance between sternal clamps 10 can be lengthened or shortened. As shown in this embodiment, first bridging member 24 comprises a pair of arm members 31 defining a central slot 32 and second bridging member 25 comprises a base member 35 with an internally-threaded screw receiving aperture (not shown). The screw receiving aperture receives screw member 27, which in combination with ridge members 28 define a link securing means 26 for securely fastening the two bridging members 24 and 25 together. In this manner the sternal clamps 10 can be properly spaced in the longitudinal direction parallel to the sternum prior to clamping the sternal halves together.

Figure 4:
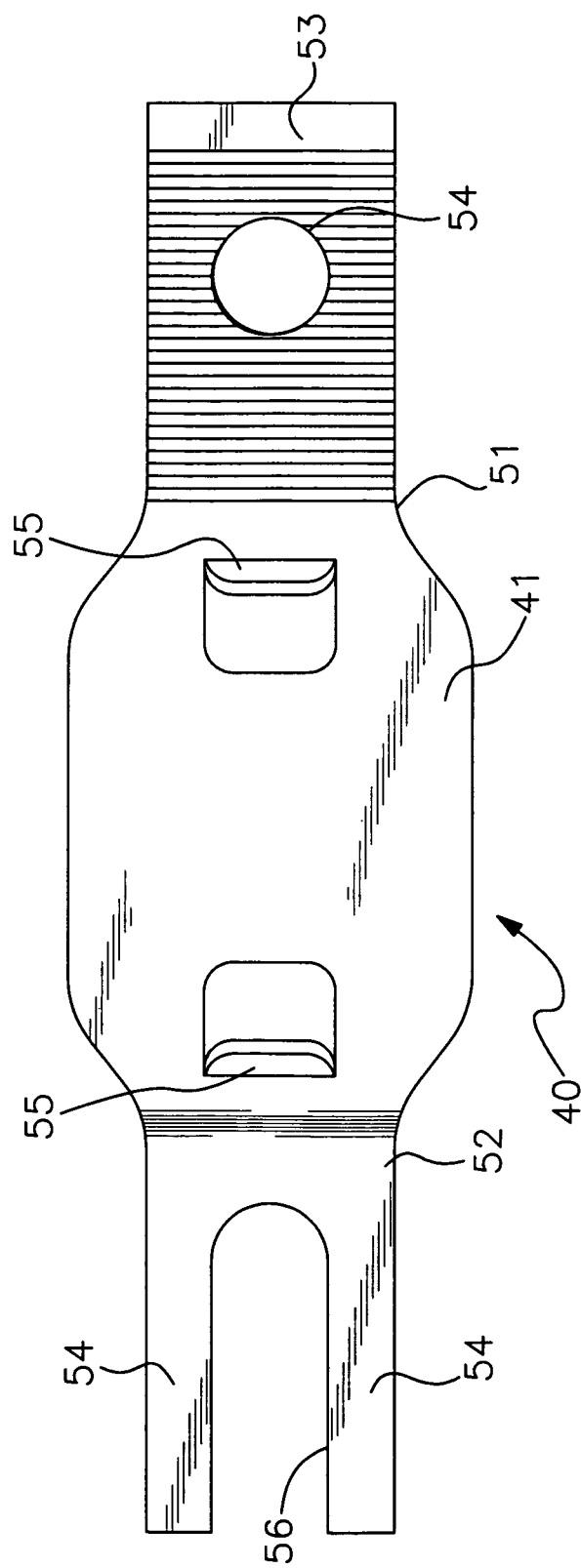
FIG. 4 is a front view of an interior clamp receiving member for use in an array containing three sternal clamps.
Figure 5:
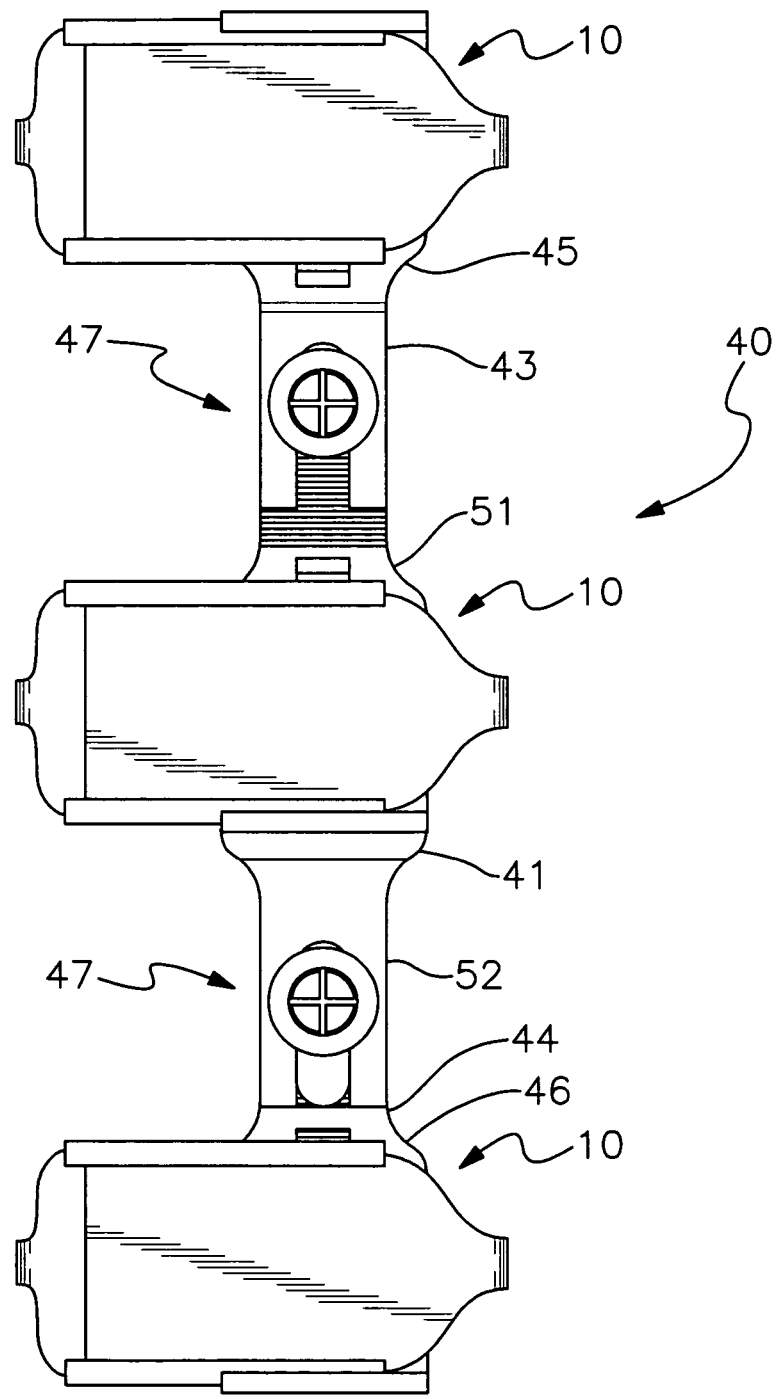
FIG. 5 is a front view of an array containing three sternal clamps.

FIGS. 4 and 5 illustrate another embodiment of the invention in which the array comprises three sternal clamps 10. In this embodiment, the linking assembly 40 comprises an interior clamp receiving member 41 having flanges 55 to retain the middle sternal clamp 10 of the grouping. The interior clamp receiving member 41 comprises first and second interior clamp bridging members 51 and 52 that extend to opposite sides of the interior clamp receiving member 41. As illustrated in this embodiment, the first interior clamp bridging member 51 comprises a base member 53 with an internally-threaded screw receiving aperture 54. The second interior clamp bridging member 52 comprises a pair of arm members 54 defining a central slot 56.

The first interior clamp bridging member 51 cooperates with the first outer clamp bridging member 43 of the first outer clamp receiving member 45, and the second interior clamp bridging member 52 cooperates with the second outer clamp bridging member 44 of the second outer clamp receiving member 46, to define clamp adjustment means for adjusting the length of the linking assemblies 40 in the same manner as clamp adjustment means 23 discussed above. Link securing means 47, as described above, are provided for joining the first and second outer clamp receiving members 45 and 46 to the first and second interior clamp bridging members 51 and 52 of interior clamp receiving member 41, such that the separation distance between the sternal clamps 10 can be adjusted as required.

It is understood that equivalents and substitutions for certain elements described above may be obvious to those of ordinary skill in the art, and therefore the true scope and definition of the invention is to be as set forth in the following claims.

We claim:

1. A sternal closure clamp device array adapted for transverse closure of a longitudinally severed sternum, said device comprising:

at least two sternal clamps each of said clamps comprising a first sliding member and a second sliding member such that the overall length of each sternal clamp is adjustable transversely across the sternum by slidably extending the first and second sliding members; and an adjustable linking assembly joining said sternal clamps, said linking assembly comprising a clamp receiving member for each sternal clamp, bridging members on each clamp receiving member, and link securing means to join said bridging members in a fixed manner;

wherein said linking assembly retains said sternal clamps in parallel and separated longitudinally along the direction of the sternum, the longitudinal distance between sternal clamps being adjustable by adjusting the length of the linking assembly.

2. The sternal closure clamp device of claim 1 wherein at least one bridging members comprises a pair of arms members defining a central slot.

3. The sternal closure clamp device of claim 2 wherein the link securing means comprises a screw receiving aperture and a plurality of ridge members.

4. The sternal closure clamp device of claim 1 wherein each clamp receiving member comprises a pair of flanges configured to retain a sternal clamp.

5. The sternal closure clamp device of claim 1 wherein the bridging members comprise a first bridging member and a second bridging member, said first bridging member and said second bridging member are disposed in a sliding relationship.

6. A sternal closure clamp device array comprising:

at least two sternal clamps, each of said clamps comprising a first sliding member having an outer end and a projection member extending rearward from the outer end of said first sliding member, and a second sliding member having an outer end and a projection member extending rearward from the outer end of said second sliding member; and at least one linking assembly configured to link said at least two sternal clamps, said linking assembly comprising a clamp receiving member for each sternal clamp, bridging members on each clamp receiving member, and link securing means to join said bridging members in a fixed manner;

wherein each clamp receiving member comprises paired flanges that secure and retain a sternal clamp, wherein one of said paired flanges comprises a lip forming a track for seating an edge of said sternal clamp, and the other of said paired flanges is a tab for abutting the opposite edge of said sternal clamp; and wherein said linking assembly retains said sternal clamps in parallel and separated longitudinally along the direction of the sternum, the longitudinal distance between sternal clamps being adjustable by adjusting the length of the linking assembly.

7. The sternal closure clamp device of claim 6 wherein at least one bridging members comprises a pair of arms members defining a central slot.

8. The sternal closure clamp device of claim 7 wherein the link securing means comprises a screw receiving aperture and a plurality of ridge members.

9. The sternal closure clamp device of claim 6 wherein each clamp receiving member comprises a pair of flanges configured to retain a sternal clamp.

10. The sternal closure clamp device of claim 6 wherein the bridging members comprise a first bridging member and a second bridging member, said first bridging member and said second bridging member are disposed in a sliding relationship.

11. A sternal closure clamp device array adapted for transverse closure of a longitudinally severed sternum, said device comprising:
- at least three sternal clamps forming a sternal clamp grouping, said sternal clamp grouping having two outer sternal clamps and at least one middle sternal clamp, wherein each of said clamps comprises a first sliding member and a second sliding member such that the overall length of each sternal clamp is adjustable transversely across the sternum by slidably extending the first and second sliding members; and
- a linking assembly configured to retain each of said sternal clamps within said grouping, said linking assembly comprising a first outer clamp receiving member having a first outer clamp bridging member, a second outer clamp receiving member having a second outer clamp bridging member, an interior clamp receiving member having a first interior clamp bridging member and a second interior clamp bridging member, and link securing means to join said bridging members in a fixed manner;
- wherein the first outer clamp receiving member is configured to retain a first outer clamp, the second outer clamp receiving member configured to retain a second outer clamp, and the interior clamp receiving member is configured to retain at least one middle clamp; and
- wherein said linking assembly retains said sternal clamps in parallel and separated longitudinally along the direction of the sternum, the longitudinal distance between sternal clamps being adjustable by adjusting the length of the linking assembly.

12. The sternal closure clamp device of claim 11 wherein said interior clamp receiving member comprises flanges configured to retain at least one middle clamp.

13. The sternal closure clamp device of claim 11 wherein said first interior clamp bridging member comprises a base member with an internally-threaded screw receiving aperture, and said second interior clamp bridging member comprises a pair of arm members defining a central slot.

14. The sternal closure clamp device of claim 13 wherein said second interior clamp bridging member is configured to cooperate with second outer clamp bridging member of the second outer clamp receiving member in a sliding relationship such that the separation distance between the sternal clamps can be adjusted.

15. The sternal closure clamp device of claim 11 wherein said first interior clamp bridging member is configured to cooperate with the first outer clamp bridging member of the first outer clamp receiving member to form clamp adjustment means.

16. The sternal closure clamp device of claim 15 wherein said first interior clamp bridging member is configured to cooperate with the first outer clamp bridging member of the first outer clamp receiving member in a sliding relationship such that the separation distance between the sternal clamps can be adjusted.

17. The sternal closure clamp of claim 11 wherein each clamp receiving member comprises paired flanges that secure and retain a sternal clamp, wherein one of said paired flanges comprises a lip forming a track for seating an edge of said sternal clamp, and the other of said paired flanges is a tab for abutting the opposite edge of said sternal clamp.

* * * * *